United States Patent
Murashita et al.

(10) Patent No.: US 8,043,266 B2
(45) Date of Patent: *Oct. 25, 2011

(54) INDWELLING NEEDLE ASSEMBLY

(75) Inventors: Takato Murashita, Nakakoma-gun (JP);
Masahiro Ishida, Nakakoma-gun (JP);
Masaki Fukuda, Nakakoma-gun (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/781,186

(22) Filed: May 17, 2010

(65) Prior Publication Data

US 2010/0228197 A1 Sep. 9, 2010

Related U.S. Application Data

(63) Continuation of application No. 11/661,597, filed as application No. PCT/JP2005/014576 on Aug. 9, 2005, now Pat. No. 7,740,614.

(30) Foreign Application Priority Data

Sep. 3, 2004 (JP) .................................. 2004-257490

(51) Int. Cl.
*A61M 5/178* (2006.01)
(52) U.S. Cl. ................................. 604/164.08
(58) Field of Classification Search ............ 604/164.01, 604/161, 164.08, 110, 160, 263, 510
See application file for complete search history.

(56) References Cited

U.S. PATENT DOCUMENTS

| | | | |
|---|---|---|---|
| 4,354,491 A | 10/1982 | Marbry | |
| 5,409,461 A | 4/1995 | Steinman | |
| 5,447,501 A | 9/1995 | Karlsson et al. | |
| 5,688,253 A | 11/1997 | Paradis | |
| 5,697,914 A | 12/1997 | Brimhall | |
| 6,749,588 B1 | 6/2004 | Howell et al. | |
| 7,247,148 B2 | 7/2007 | Murashita | |
| 2001/0027292 A1 | 10/2001 | Tamura et al. | |
| 2002/0177812 A1 | 11/2002 | Moulton et al. | |

(Continued)

FOREIGN PATENT DOCUMENTS

CN 1501822 A 6/2004

(Continued)

OTHER PUBLICATIONS

Extended European Search Report issued in corresponding EP Patent Application No. 05 77 0366, Jul. 4, 2008, EPO, Berlin, DE.
Murashita, et al., CN Grant Announcement No. CN100475285C, Apr. 8, 2009, Chinese State Intellectual Property Office, Peoples Republic of China.

(Continued)

*Primary Examiner* — Nicholas D Lucchesi
*Assistant Examiner* — Brooke Matney
(74) *Attorney, Agent, or Firm* — Buchanan Ingersoll & Rooney PC

(57) ABSTRACT

An indwelling needle assembly has an inner needle having a sharp point at its tip, an inner needle hub fixed to a base section of the inner needle, a hollow outer needle into which the inner needle is inserted, an outer needle hub fixed to a base section of the outer needle, and a tube inserted into the inner needle hub and connected to the base section of the outer needle hub such that the inner cavity of the tube communicates with the inner cavity of the outer needle. The center axis of the outer needle and the center axis of the tube at its head section are substantially parallel with each other with the inner needle inserted into the outer needle.

10 Claims, 7 Drawing Sheets

U.S. PATENT DOCUMENTS

| | | |
|---|---|---|
| 2002/0177814 A1 | 11/2002 | Meng et al. |
| 2004/0097880 A1 | 5/2004 | Schur |
| 2004/0225260 A1 | 11/2004 | Villa et al. |

FOREIGN PATENT DOCUMENTS

| | | |
|---|---|---|
| JP | 2-147137 U | 12/1990 |
| JP | 8-257129 U | 10/1996 |
| JP | 10-179734 A | 7/1998 |
| JP | 11-089939 A | 4/1999 |
| JP | 2000-014769 A | 1/2000 |
| JP | 2000-116791 A | 4/2000 |
| JP | 2004-057516 A | 2/2004 |
| JP | 2004-073403 A | 3/2004 |

OTHER PUBLICATIONS

Communication of a Notice of Opposition and Notice of Opposition issued in EP Patent No. 1 790 372 (EP Patent Application No. 05 770 366.2), Jun. 29, 2010, 28 pages, European Patent Office, Berlin, DE.

Communication of Notices of Opposition issued in EP Patent No. 1 790 372 (EP Patent Application No. 05 770 366.2), Jul. 26, 2010, 1 page, European Patent Office, Berlin, DE.

INDWELLING NEEDLE ASSEMBLY

The present application is a Continuation Application of U.S. application Ser. No. 11/661,597, file Mar. 1, 2007, which is the National Stage of International Application No. PCT/JP2005/014576, filed Aug. 9, 2005, and claims foreign priority to Japanese Application No. 2004-257490, filed Sep. 3, 2004, the entire contents of each of which are incorporated by reference herein.

TECHNICAL FIELD

The present invention relates to an indwelling needle assembly made to puncture a blood vessel and indwell there at the time of, for example, infusion.

BACKGROUND ART

In the case of infusion to a patient or the like occasion, an indwelling needle connected to an infusion line is stuck into a blood vessel of the patient and indwells there.

Such an indwelling needle includes a hollow outer needle, an outer needle hub fixed to the base of the outer needle, an inner needle having a sharp point at its tip and inserted into the outer needle, and an inner needle hub fixed to the base of the inner needle.

At the time of puncturing a patient's blood vessel with the indwelling needle, the inner needle is inserted into the outer needle, the needle point of the inner needle is protruded from the tip of the outer needle, and, in this assembled condition, the puncturing operation is carried out.

Then, when the needle point of the inner needle has reached the inside of the blood vessel, the blood flowing in through the opening at the needle point passes through the inner cavity of the inner needle, and flows into the inside of the transparent inner needle hub (flush-back). This makes it possible to confirm (visually check) that the inner needle has captured the blood vessel.

After confirmation of the flush-back, the inner needle and the outer needle are slightly moved forwards to insert the tip of the outer needle into the blood vessel.

Next, while gripping the outer needle by hand, the inner needle is pulled out of the outer needle, and a connector of the infusion line is connected to the outer needle hub. Then, an infusion liquid is infused through the connected infusion line and the outer needle.

Meanwhile, at the time of pulling off the outer needle from the inner needle, it is necessary to hold the conduit of the outer needle in a closed state, for preventing the blood from flowing out through the base of the outer needle hub. This is a very troublesome operation.

As a solution to such a problem, for example, Japanese Laid-Open Patent Publication No. 10-179734 discloses an indwelling needle. A tube of an infusion line or the like is preliminarily connected to an outer needle hub.

In this indwelling needle, however, the tube is connected to a lateral side of the outer needle hub, and, therefore, the tube serves as an obstacle at the time of the puncturing operation, leading to poor operationality.

DISCLOSURE OF THE INVENTION

It is an object of the present invention to provide an indwelling needle assembly which is excellent in operationality at the time of a puncturing operation.

In order to attain the above object, according to the present invention, there is provided an indwelling needle assembly including:
  an inner needle having a sharp point at its tip;
  an inner needle hub fixed to a base section of the inner needle;
  a hollow outer needle into which the inner needle is inserted;
  an outer needle hub fixed to a base section of the outer needle; and
  a tube inserted into the inner needle hub and connected to the base section of the outer needle hub so that the inner cavity of the tube communicates with the inner cavity of the outer needle. The center axis of the outer needle and the center axis of the tube at its head section are substantially parallel with each other in the condition where the inner needle is inserted into the outer needle.

This ensures excellent operationality and makes it possible to secure the line for infusion or the like easily and assuredly, since the tube would not serve as an obstacle at the time of the puncturing operation.

In addition, the indwelling needle assembly according to the present invention, preferably, further includes a seal member provided at the outer needle hub, provided with a hole into which the inner needle can be inserted, and having a self-closing property such that the hole closes upon withdrawal of the inserted inner needle.

This makes it possible to prevent leakage of liquid from the base of the outer needle hub upon withdrawal of the inner needle, and also to maintain the inside of the outer needle hub in an aseptic condition.

Besides, in the indwelling needle assembly of the present invention, preferably, the inner needle has a section differing in an outside diameter; and a smallest outside diameter section of the inner needle is located in the hole of the seal member in the condition where the inner needle is inserted in the outer needle.

This makes it possible to prevent the sealing performance of the seal member from being lowered due to a permanent or semi-permanent deformation thereof.

In addition, in the indwelling needle assembly of the present invention, preferably, the inner cavity of the outer needle and the inner cavity of the tube communicate with each other through a junction conduit provided in the outer needle hub; and the junction conduit is completed by communication between a conduit formed in the seal member and a conduit formed in a side wall part of the outer needle hub.

This makes it possible to make the junction conduit comparatively short, and to prevent the outer needle hub from being enlarged in size.

Besides, in the indwelling needle assembly of the present invention, preferably, the inner cavity of the outer needle and the inner cavity of the tube communicate with each other through a junction conduit provided in the outer needle hub.

This makes it possible to make the junction conduit comparatively short.

In addition, in the indwelling needle assembly of the present invention, preferably, the junction conduit has a substantially L-shaped part.

This makes it possible to make the junction conduit comparatively small in length.

Besides, the indwelling needle assembly of the present invention, preferably, further includes a protector for covering at least the point of the inner needle when the inner needle is withdrawn from the outer needle, with the protector being located on the base side relative to the seal member in the condition where the inner needle is inserted in the outer needle.

This eliminates the need to pass the protector through the hole in the seal member at the time of withdrawing the inner needle from the outer needle, so that the withdrawing operation can be carried out easily and assuredly. Besides, the overall length of the inner needle can be set shorter, so that it can be contrived to reduce the size of the indwelling needle assembly exclusive of the tube.

In addition, the indwelling needle assembly of the present invention, preferably, has a protector for covering at least the tip of the inner needle when the inner needle is withdrawn from the outer needle.

This prevents the worker or the like from erroneously piercing his finger or the like with the needle point during an inner needle discarding work or the like; thus, high safety is ensured.

Besides, in the indwelling needle assembly of the present invention, preferably, the protector is substantially entirely covered with the inner needle hub and/or the outer needle hub in the condition where the inner needle is inserted in the outer needle.

This ensures that the puncturing with the outer needle and the inner needle can be carried out more assuredly, since the protector would not serve as an obstacle.

In addition, in the indwelling needle assembly of the present invention, preferably, the protector includes a protector body having an inner needle passage into which the inner needle can be inserted, and shutter means which is displaced between a first posture such that the inner needle can be inserted into the inner needle passage and a second posture such as to inhibit the passage of the needle point of the inner needle.

This prevents the worker or the like from erroneously piercing his finger or the like with the needle point during an inner needle discarding work or the like; thus, high safety is ensured.

Besides, the indwelling needle assembly of the present invention, preferably, has fixing means for fixing the protector to the outer needle hub.

This makes it possible to fix the protector to the outer needle hub assuredly.

In addition, in the indwelling needle assembly of the present invention, preferably, the fixing means is so configured that the fixation of the protector to the outer needle hub can be maintained in the condition where the shutter means is operated.

This ensures that the shutter means can be operated securely in the condition where the fixation of the protector to the outer needle hub is released. Therefore, it is possible to securely prevent the accident in which the worker or the like might erroneously pierce his finger or the like with the needle point during an inner needle discarding work or the like.

Besides, the indwelling needle assembly of the present invention, preferably, has movement restraining means for restraining the inner needle from moving in the direction opposite to its point in relation to the protector in the condition where the protector covers at least the point of the inner needle.

This prevents the inner needle from coming off from the protector in the state of covering the needle point.

In addition, in the indwelling needle assembly of the present invention, preferably, the movement restraining means comprises engaging means for engagement between the inner needle and the protector.

This ensures that, in a series of operations for withdrawing the inner needle from the outer needle, the inner needle can be engaged with the protector and the protector can be detached from the outer needle hub; therefore, the series of operations can be carried out extremely readily. In addition, the inner needle is prevented from coming off from the protector in the state of covering the needle point.

Besides, in the indwelling needle assembly of the present invention, preferably, the inner needle has a section differing in an outside diameter;

the protector body has a reduced diameter section where the inside diameter of the inner needle passage is reduced; and the engaging means comprises the section with a varying outside diameter of the inner needle and the reduced diameter section.

This ensures that, in a series of operations for withdrawing the inner needle from the outer needle, the inner needle can be engaged with the protector and the protector can be detached from the outer needle hub. Therefore, the series of operations can be carried out extremely readily. Besides, the inner needle can be prevented from coming off from the protector in the state of covering the needle point.

In addition, in the indwelling needle assembly of the present invention, preferably, a conduit providing communication between the tip opening of the outer needle and the inside of the outer needle hub is formed in at least a part, making close contact with the outer needle, of an outer peripheral portion of the inner needle in the condition where the inner needle is inserted into the outer needle.

This ensures that the blood (body fluid) at the time of puncturing a blood vessel, for example, can pass through the conduit.

Besides, in the indwelling needle assembly of the present invention, preferably, the inner needle has at its tip section a part making close contact with the outer needle.

This ensures that the blood (body fluid) at the time of puncturing a blood vessel, for example, can pass through the conduit assuredly.

In addition, in the indwelling needle assembly of the present invention, preferably, the inner needle is solid.

This makes it possible to secure a sufficient strength while setting the small outside diameter of the inner needle. In addition, at the time of discarding the inner needle after completion of the procedure, there is no danger of remaining of the blood inside the inner needle or flowing-out of the blood; thus, high safety is ensured.

Besides, in the indwelling needle assembly of the present invention, preferably, the inner needle hub is provided with a slit along its longitudinal direction, so that the tube can be detached from the inner needle hub through the slit when the inner needle is withdrawn from the outer needle.

This makes it possible to detach the tube from the inner needle hub easily and assuredly when the inner needle is withdrawn from the outer needle.

BEST MODE FOR CARRYING OUT THE INVENTION

Now, an indwelling needle assembly according to the present invention will be described in detail below, based on a preferred embodiment shown in the accompanying drawings.

Figure 1:
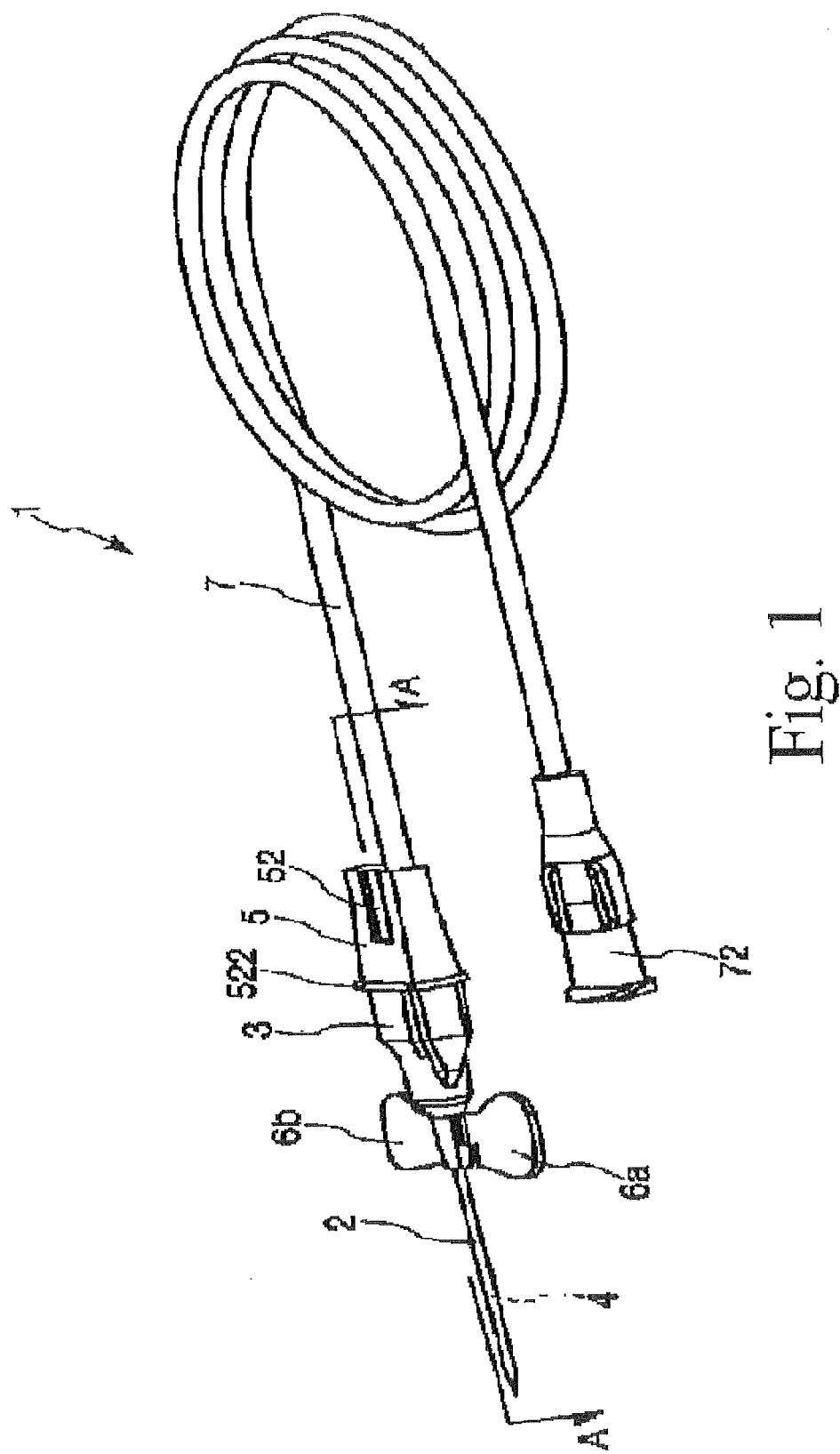
FIG. 1 is a perspective view showing an embodiment of an indwelling needle assembly according to the present invention.
Figure 3:
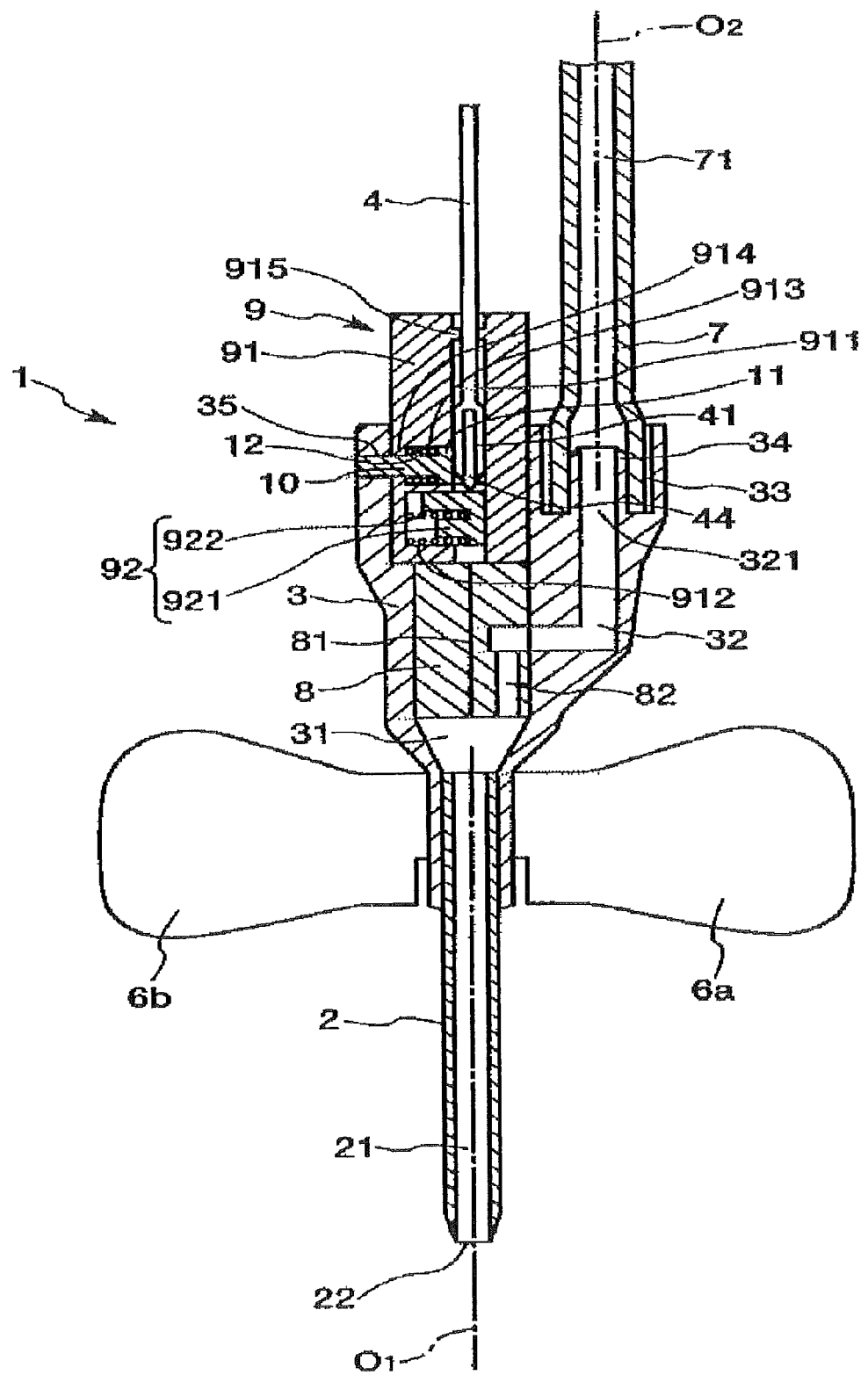
FIG. 3 is a sectional view along the line A-A in FIG. 1.
Figure 4:
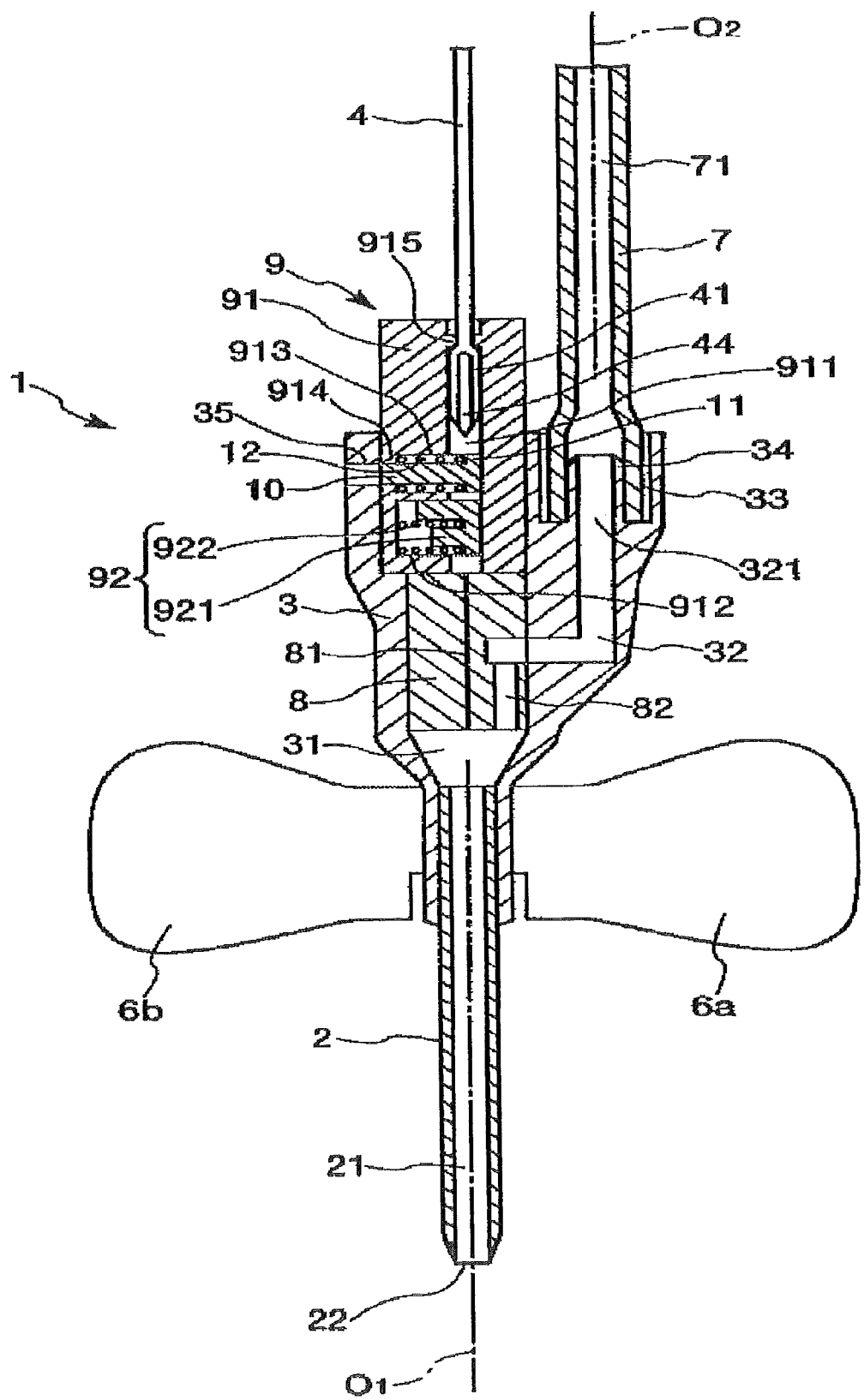
FIG. 4 is a sectional view along the line A-A in FIG. 1.
Figure 5:
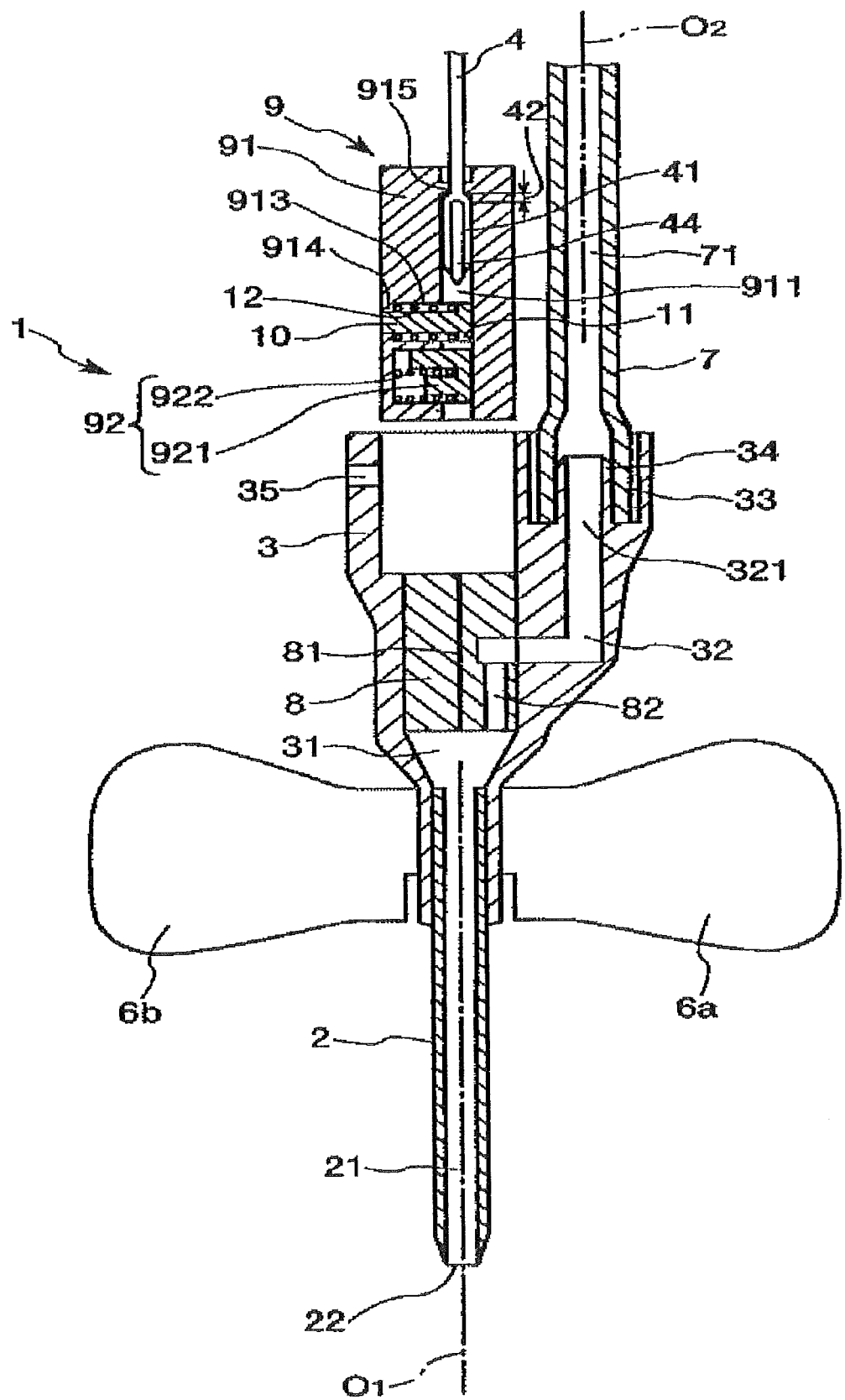
FIG. 5 is a sectional view along the line A-A in FIG. 1.
Figure 6:
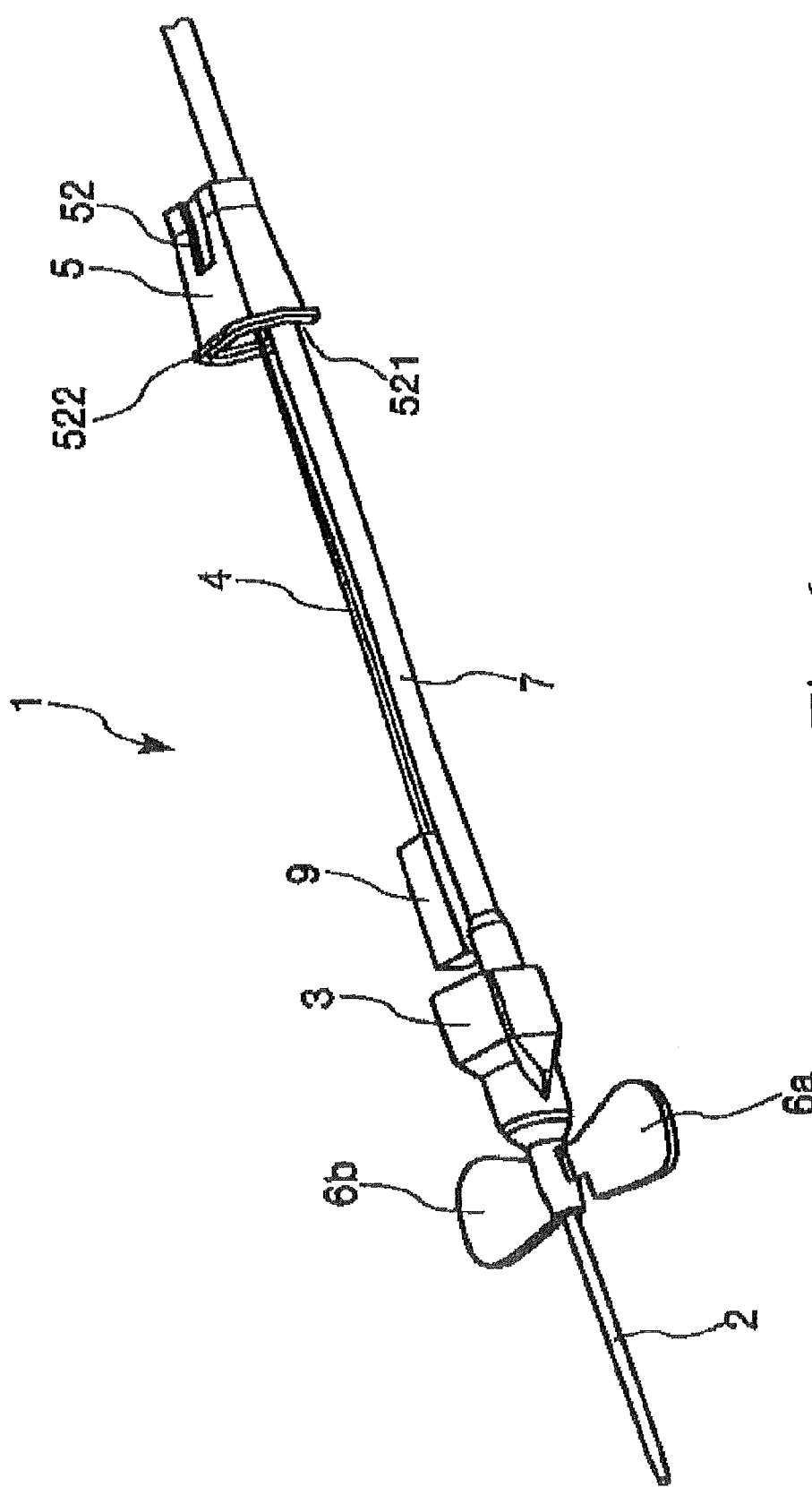
FIG. 6 is a perspective view, corresponding to FIG. 5, of the indwelling needle assembly shown in FIG. 1.
Figure 7:
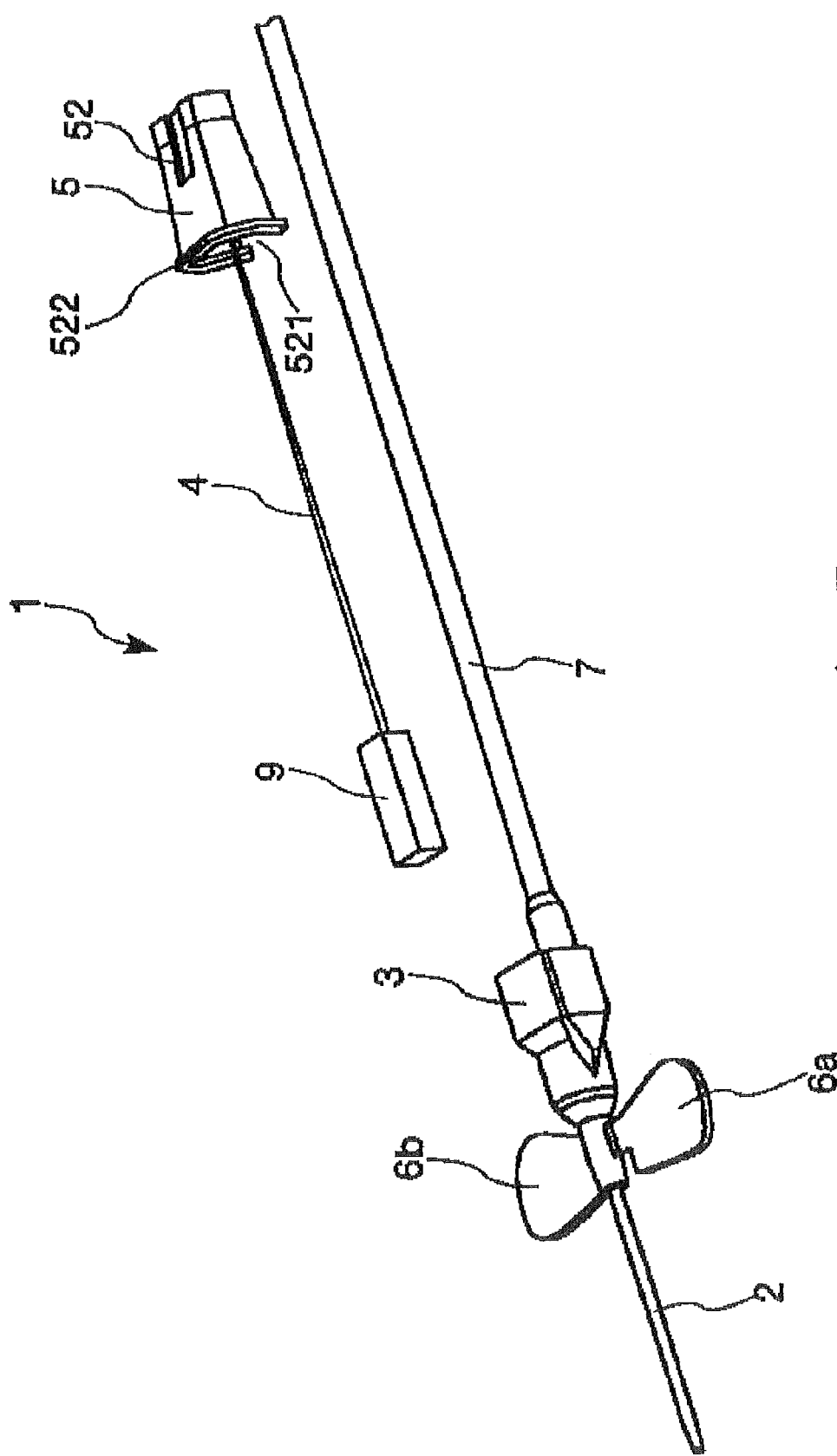
FIG. 7 is a perspective view showing the condition where a tube is detached from an inner needle hub, of the indwelling needle assembly shown in FIG. 1.

FIG. 1 is a perspective view showing an embodiment of the indwelling needle assembly according to the present invention, FIGS. 2 to 5 are sectional views along a line A-A in FIG. 1, FIG. 6 is a perspective view, corresponding to FIG. 5, of the indwelling needle assembly shown in FIG. 1, and FIG. 7 is a perspective view showing the condition where a tube is detached from an inner needle hub, of the indwelling needle assembly shown in FIG. 1.

Incidentally, in the following description, the right side in FIGS. 1, 6 and 7 will be referred to as "the base", and the left side as "the tip"; besides, the upper side in FIGS. 2 to 5 will be referred to as "the base", and the lower side as "the tip".

The indwelling needle assembly 1 shown in the figures includes a hollow outer needle 2, an outer needle hub 3 fixed to a base section of the outer needle 2, an inner needle 4 inserted into the outer needle 2, an inner needle hub 5 fixed to a base section of the inner needle 4, and a tube 7 connected to a base section of the outer needle hub 3 so that its inner cavity 71 communicates with the inner cavity 21 of the outer needle 2. Now, the configurations of these components and sections will be described below.

As the outer needle 2, one having a certain degree of flexibility is used. The material constituting the outer needle 2 is preferably a resin material, particularly a soft resin material. Specific examples of the material includes fluoro-resins such as PTFE, ETFE, PFA, etc., olefin resins such as polyethylene, polypropylene, etc. and mixtures thereof, polyurethane, polyester, polyamide, polyether nylon resins, mixtures of the olefin resin with ethylene-vinyl acetate copolymer, etc.

Of the outer needle 2 as above, the whole part or a part may have such a property that its inside can be visually confirmed. In addition, the material constituting the outer needle 2 may be admixed with a radiopaque contrast agent such as barium sulfate, barium carbonate, bismuth carbonate, tungstic acid, etc., to obtain a contrast property.

The outer needle hub 3 is fixed liquid-tightly to a base section of the outer needle 2 by such a method as caulking, fusing (heat fusing, high-frequency fusing or the like), adhesion with an adhesive, etc.

The outer needle hub 3 is composed of a substantially tubular member, and its inside 31 communicates with the inner cavity 21 of the outer needle 2.

Figure 2:
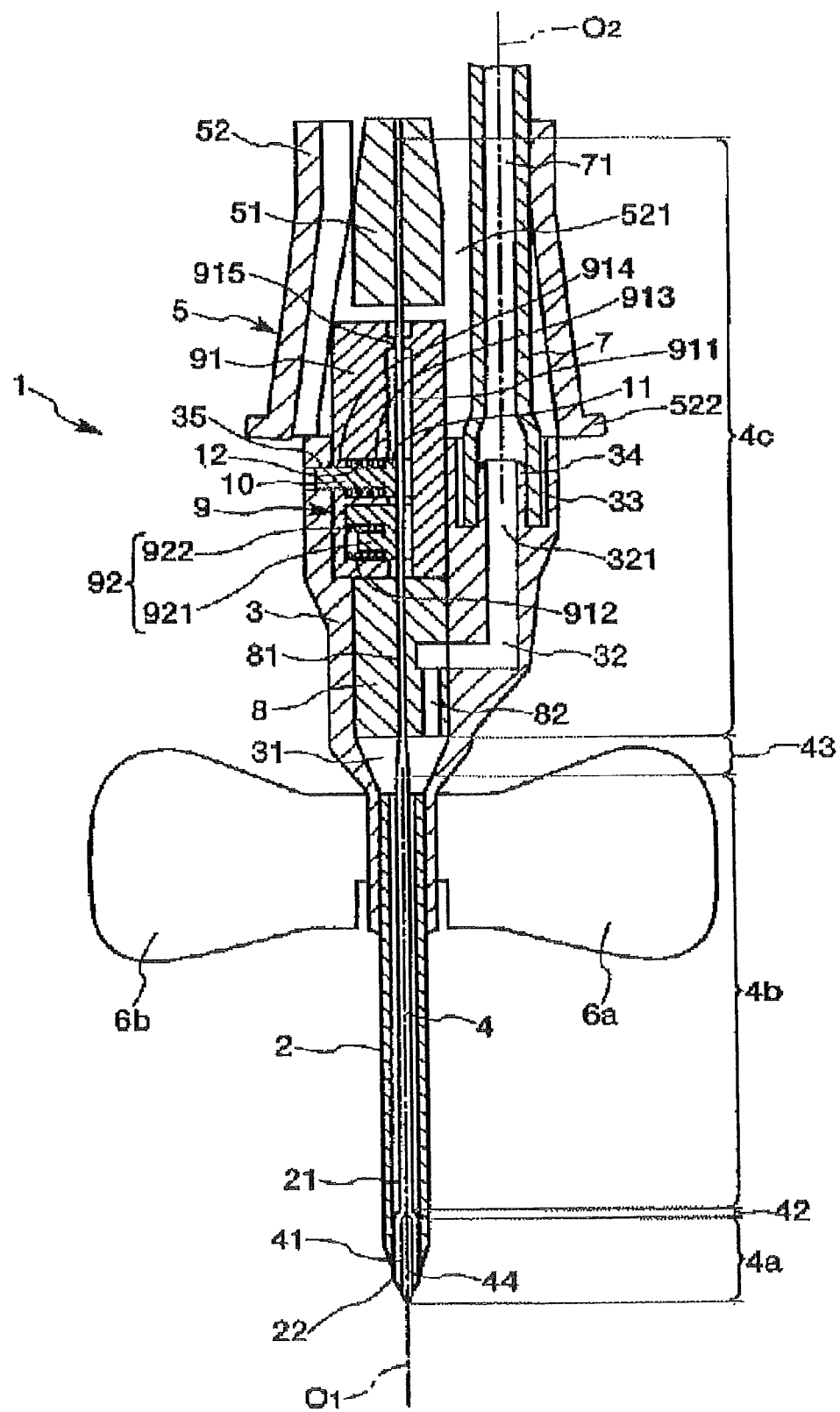
FIG. 2 is a sectional view along a line A-A in FIG. 1.

A wall part on the right side in FIG. 2 (and in FIGS. 3 to 5, also) of the outer needle hub 3 is provided therein with a conduit 32 which opens at its one end into the inside 31 of the outer needle hub 3. The conduit 32 is substantially L-shaped, and the other end thereof opens at a recessed part 33 formed in the base of the outer needle hub 3, to form an opening 321. In addition, at the tip face (bottom face) of the recessed part 33, a projected part (connecting part) 34 in an annular shape surrounding the opening 321 is formed to be projected in the base direction.

The projected part 34 is inserted into the inner cavity 71 of the tube 7 at the head of the tube 7, and one end of the tube 7 is connected to the outer needle hub 3.

Besides, on the left and right sides of the outer needle hub 3 in FIG. 2, a pair of vanes 6a and 6b are formed to be integral with the outer needle hub 3. The vanes 6a and 6b are flexible, and are so configured that they can be opened and closed through bending or curving in the vicinity of joint parts between the vanes 6a, 6b and the outer needle hub 3.

At the time of puncturing a blood vessel or the like with the outer needle 2 and the inner needle 4, the vanes 6a and 6b are pinched with fingers to bring them into a closed condition, and then the puncturing operation can be conducted. Besides, instead of pinching the vanes 6a and 6b, the inner needle hub 5 may be pinched with the thumb and the middle finger, be made to puncture the blood vessel, and after the tip of the outer needle 2 is inserted into the blood vessel, the outer needle hub 3 may be pushed forward by the index finger, to move only the outer needle 2 into the blood vessel. At the time of causing the outer needle 2 to indwell, the vanes 6a and 6b are put into the opened condition, and the vanes 6a and 6b are fixed to the skin with a pressure sensitive adhesive tape or the like.

The inner needle 4 having a sharp point 41 at its tip is inserted into the outer needle 2. The indwelling needle assembly 1 is used in the condition where the inner needle 4 is inserted in the outer needle 2 and the inner needle hub 5 (described later) and the outer needle hub 3 are in contact with each other, i.e., in the condition shown in FIGS. 1 and 2. Hereinafter, this condition will be referred to as "the assembled condition".

The length of the inner needle 4 is set at such a level that at least the needle point 41 thereof protrudes from the tip opening 22 of the outer needle 2 in the assembled condition.

The inner needle 4 may be a hollow needle, but it is preferably a solid needle. Where the inner needle 4 is a solid needle, a sufficient strength can be secured while its outside diameter being set to be small. Besides, where the inner needle 4 is solid, the danger of remaining of the blood in the inside of the inner needle 4 or flowing-out of the blood, at the time of discarding the inner needle 4 after completion of the procedure, can be excluded; thus, high safety is ensured.

Incidentally, the inner needle 4 may be configured to have both a hollow section and a solid section (for example, hollow on the tip side and solid on the base side). However, by composing the whole part of the inner needle 4 of a single member, a reduction in the cost of the inner needle 4 can be contrived.

In addition, the inner needle 4 has a plurality (three, in this embodiment) of sections differing in outside diameter from each other. Specifically, the inner needle 4 has a maximum outside diameter section 4a, having a maximum outside diameter, on the tip side (tip section), a minimum outside diameter section 4c, having a minimum outside diameter, on the base side, and an intermediate outside diameter section 4b between the maximum outside diameter section 4a and the minimum outside diameter section 4c, having a diameter between the diameter of the section 4a and the diameter of the section 4c.

As a result, the inner needle 4 is provided with a first varied outside diameter section 42 (continuously varied in outside diameter) at the boundary between the maximum outside diameter section 4a and the intermediate outside diameter section 4b, and with a second varied outside diameter section 43 (continuously varied in outside diameter) between the intermediate outside diameter section 4b and the minimum outside diameter section 4c.

At each of the varied outside diameter sections 42 and 43, the outside diameter of the inner needle 4 may be varied stepwise. However, when the outside diameter of the inner needle 4 is continuously varied in outside diameter (is tapered), each of the varied outside diameter sections 42 and 43 can be prevented from being caught by a tip edge part of the hole 81 in the seal member 8 (described later), a tip edge part of an inner needle passage 911 in a protector body 91, or the like at the time of withdrawing the inner needle 4 from the outer needle 2. Therefore, the operation of withdrawing the inner needle 4 from the outer needle 2 can be carried out more smoothly and assuredly.

Incidentally, the varied outside diameter sections 42 and 43 may be formed at the time of producing the inner needle 4, and alternatively, a step or steps inevitably formed at the time of forming a groove 44 (described later) may be utilized.

In addition, the maximum outside diameter section 4a has an outside diameter set to be approximately equal to the inner diameter of the outer needle 2, so that it makes close contact with the inside surface of the outer needle 2 in the condition where the inner needle 4 is inserted in the outer needle 2. An outer peripheral part of the maximum outside diameter section 4a is provided with the groove (conduit) 44 in a recessed form along the longitudinal direction of the inner needle 4. The groove 44 provides communication between the tip opening 22 of the outer needle 2 and the inside 31 of the outer needle hub 3 in the condition where the inner needle 4 is inserted in the outer needle 2. The groove 44 functions as a conduit for the blood (body fluid), at the time of puncturing a blood vessel, for example.

Examples of the material constituting the inner needle 4 as above include metallic materials such as stainless steel, aluminum, aluminum alloys, titanium, titanium alloys, etc.

The inner needle hub 5 is fixed to a base section of the inner needle 4. The inner needle hub 5 is composed of a fixing section 51 for fixing the inner needle 4, and a cover section 52 provided on the outer periphery side of the fixing section 51. Preferably, the fixing section 51 and the cover section 52 are formed integrally.

In addition, the tube 7 is disposed between the fixing section 51 and the cover section 52. Namely, the tube 7 is inserted in the inner needle hub 5.

The fixation of the inner needle 4 to the inner needle hub 5 (the fixing section 51) may be carried out by such a method as fitting, caulking, fusing, adhesion with an adhesive, etc. or by a combination of these method. Besides, in the case where the inner needle 4 is hollow, it is necessary, for example, to seal the inner needle 4 such that the blood flowing back upon puncturing a blood vessel with the inner needle 4 will not run out through the base of the inner needle 4.

The cover section 52 is provided with a slit 521 along its longitudinal direction, and is roughly angular U-shaped in cross section. Upon withdrawal of the inner needle 4 from the outer needle 2, the tube 7 can be detached from the inner needle hub 5 through the slit 521.

In addition, a flange 522 is provided at the outer periphery of the tip of the inner needle hub 5. For example, at the time of withdrawing the inner needle 4 from the outer needle 2, fingers may be put on the flange 522 to thereby perform the withdrawing operation, whereby the operation can be carried out easily and assuredly.

The inner needle hub 5 and the above-described outer needle hub 3 are preferably formed from a transparent (colorless transparent), colored transparent or semi-transparent resin, to secure a property such that the inside can be visually confirmed. This ensures that, when the outer needle 2 has captured a blood vessel, the flush-back of the blood flowing in through the groove 44 of the inner needle 4 as above-mentioned can be visually confirmed. In addition, where the inner needle 4 is solid, all the blood in flush-back under the pressure inside a blood vessel, for example, flows back through the groove 44, which enhances the visual confirmability.

The materials constituting the outer needle hub 3, the inner needle hub 5 and the vanes 6a and 6b are not particularly limited. Examples of the materials include various resin materials such as polyolefins such as polyethylene, polypropylene, ethylene-vinyl acetate copolymer, etc., polyurethane, polyamides, polyesters, polycarbonate, polyvinyl chloride, etc.

The tube 7 is flexible and, as above-mentioned, its one end is connected to the base section of the outer needle hub 3. To the other end of the tube 7, a connector 72 is mounted. To the connector 72 is connected, for example, a connector mounted to an end of an infusion line for supplying an infusion liquid (liquid medicine) to be dosed or a mouth (tip section) of a syringe in which a liquid medicine is contained.

Besides, the indwelling needle assembly 1 has a block-like seal member 8 in the inside 31 of the outer needle hub 3. The seal member 8 is provided substantially in the center thereof with a hole 81 penetrating the seal member 8 along its longitudinal direction. The center axis of the hole 81 and the center axis $O_1$ of the outer needle 2 substantially coincide with each other.

The seal member 8 has a self-closing property such that when the inner needle 4 inserted in the hole 81 in the assembled condition is withdrawn, the hole 81 is closed by the elasticity of the seal member 8 itself. This ensures that, upon withdrawal of the inner needle 4, the leakage of a liquid through the base of the outer needle hub 3 can be prevented, and the asepsis of the inside of the outer needle hub 3 can be maintained.

In addition, in the assembled condition, the minimum outside diameter section 4c of the inner needle 4 is located in the hole 81. This configuration makes it possible to prevent the seal member 8 from being deformed permanently or semi-permanently to lower sealing performance.

Examples of the material constituting the seal member 8 include various elastic materials such as various rubber materials (particularly those vulcanized) such as natural rubber, isoprene rubber, butyl rubber, butadiene rubber, styrene-butadiene rubber, urethane rubber, nitrile rubber, acrylic rubber, fluoro-rubber, silicone rubber, etc., various thermoplastic elastomers based on urethane, polyester, polyamide, olefin, styrene, etc. and mixtures thereof.

Besides, the seal member 8 is provided with a conduit 82 at a location different from that of the hole 81. The conduit 82 is opened in the tip face and a side surface of the seal member 8, and is roughly L-shaped.

When the seal member 8 is inserted into the outer needle hub 3 and an opening where the conduit 82 is opened in the side surface of the seal member 8 and an opening where the above-mentioned conduit 32 is opened into the inside 31 of the outer needle hub 3 are set to coincide with each other, a crank-shaped junction conduit is formed (completed). The junction conduit provides communication between the inner cavity 21 of the outer needle 2 and the inner cavity 71 of the tube 7. This configuration makes it possible to make the junction conduit comparatively short and to prevent the outer needle hub 3 from being enlarged in size.

Furthermore, the indwelling needle assembly 1 has a protector 9 for covering at least the needle point 41 of the inner needle 4 when the inner needle 4 is withdrawn from the outer needle 2. The protector 9 will be described in detail below.

As shown in FIGS. 2 to 5, the protector 9 includes a protector body 91 having a substantially rectangular parallelepiped outer shape, and shutter means 92 provided in the protector body 91.

Substantially in the center of the protector body 91, an inner needle passage 911 in which the inner needle 4 is inserted is formed to penetrate the protector body 91 along the longitudinal direction of the protector body 91.

The inner needle passage 911 is substantially circular in cross sectional shape, and its inside diameter is equal to or slightly greater than the outside diameter of the inner needle 4 (the maximum outside diameter section 4a).

In addition, the inside wall (the surface fronting on the inner needle passage 911) on the tip side of the protector body 91 is provided with a recessed part 912.

The shutter means 92 is stored in the recessed part 912. The shutter means 92 is composed of a block-shaped shutter member 921, and a coil spring (urging means) 922 for urging the shutter member 921 toward the inner needle passage 911.

The shutter means 92 can be displaced between a first posture (the posture shown in FIG. 2) such that the most part of the shutter means 92 is retracted into the recessed part 912 and the inner needle 4 can be inserted in the inner needle passage 911 and a second posture (the posture shown in FIG. 3) such that a part of the shutter member 921 enters the inner needle passage 911 to inhibit the passage of the needle point 41 of the inner needle 4.

With the protector 9 as above, the needle point 41 of the inner needle 4 after use can be covered by a simple operation speedily and safely. In addition, due to the action of the shutter means 92, the needle point 41 once covered is prevented from protruding from the tip of the protector 9 (the protector body 91). Therefore, an accident in which the worker or the like might erroneously pierce his finger or the like with the needle point 41 in discarding the inner needle 4 or the like occasion is prevented, and high safety is thereby ensured.

Besides, in the assembled condition, substantially the whole part of the protector 9 is covered with both the outer needle hub 3 and the inner needle hub 5. This ensures that the protector 9 does not obstruct the puncturing with the outer needle 2 and the inner needle 4, so that the puncturing operation can be performed more assuredly. Incidentally, the protector 9 may be substantially wholly covered with either one of the outer needle hub 3 and the inner needle hub 5.

Furthermore, the protector 9 is so configured as to be located on the base side relative to the seal member 8 in the assembled condition. This eliminates the need to pass the protector 9 through the hole 81 in the seal member 8 at the time of withdrawing the inner needle 4 from the outer needle 2, and therefore the withdrawing operation can be performed more easily and securely. In addition, this configuration makes it possible to set the overall length of the inner needle 4 to be shorter, whereby a reduction in the size of the part exclusive of the tube 7 of the indwelling needle assembly 1 can be contrived.

Besides, the indwelling needle assembly 1 as above has fixing means for fixing the protector 9 to the outer needle hub 3, and engaging means (movement restraining means) for restraining the inner needle 4 from moving in the direction opposite to the needle point 41 in relation to the protector 9, by engagement between the inner needle 4 and the protector 9, in the condition where at least the needle point 41 of the inner needle 4 is covered with the protector 9. Now, the fixing means and the engaging means will be described in detail below.

<Fixing Means>

First, the fixing means will be described.

The inside wall of the protector body 91 is provided with a through-hole 913 on the base side of the recessed part 912, and a projected part 914 projected toward the inside is formed at the left end, in FIG. 2, of the through-hole 913.

A fixing pin 10 having a flange part 11 at its right end in FIG. 2 is inserted in the through-hole 913, in the condition where a coil spring 12 is stored. In this condition, the left end of the coil spring 12 in FIG. 2 is in contact with the projected part 914, and the right end in FIG. 2 is in contact with the flange part 11.

In addition, a through-hole 35 into which the fixing pin 10 can be inserted is formed in a base section of the left side wall part of the outer needle hub 3 in FIG. 2.

In the condition where the inner needle 4 is inserted in (penetrates) the inner needle passage 911, the right surface of the fixing pin 10 in FIG. 2 is in contact with the outer peripheral surface of the inner needle 4, and the left end part of the fixing pin 10 in FIG. 2 is protruded from the through-hole 913 and inserted in the through-hole 35. In this way, the protector 9 is fixed to the outer needle hub 3 (see FIGS. 2 and 3).

On the other hand, when the inner needle 4 is withdrawn from the inner needle passage 911, the fixing pin 10 is pushed by the coil spring 12 to move toward the right side in FIG. 4, and the left end part of the fixing pin 10 in FIG. 2 comes out of the through-hole 35. In this way, the fixation of the protector 9 to the outer needle hub 3 is cleared (see FIG. 4).

Thus, in the present embodiment, the fixing means for fixing the protector 9 to the outer needle hub 3 is composed mainly of the through-hole 913, the fixing pin 10, the coil spring 12 and the inner needle 4.

Besides, as shown in FIG. 3, in this embodiment, the fixing means operates after the operation of the shutter means 92. Specifically, the fixation of the protector 9 to the outer needle hub 3 by the fixing means is maintained in the condition where the shutter means 92 has operated. This configuration ensures that the shutter means 92 is operated assuredly in the condition where the fixation of the protector 9 to the outer needle hub 3 is released. Therefore, the accident in which the worker or the like might erroneously pierce his finger or the like with the needle point 41 in discarding the inner needle 4 or the like occasion can be prevented securely.

<Engaging Means>

Now, the engaging means will be described below.

A base section of the protector body 91 is provided with a reduced diameter part 915 where the inner needle passage 911 is reduced in diameter. The inside diameter of the reduced diameter part 915 is greater than the outside diameters of the intermediate outside diameter section 4b and the minimum outside diameter section 4c of the inner needle 4, and is smaller than the outside diameter of the maximum outside diameter section 4a.

This ensures that, at the time of withdrawing the inner needle 4 from the outer needle 2, the minimum outside diameter section 4c, the second varied outside diameter section 43 and the intermediate outside diameter section 4b can pass through the reduced diameter part 915, but the first varied outside diameter section 42 cannot pass through the reduced diameter part 915, so that it is engaged with the reduced diameter part 915 (see FIG. 4).

In other words, in this embodiment, the first varied outside diameter section 42 and the reduced diameter part 915 constitute the engaging means for engagement between the inner needle 4 and the protector 9.

With the engaging means provided, in a series of operations for withdrawing the inner needle 4 from the outer needle 2, it is possible to engage the inner needle 4 with the protector 9 and to release the protector 9 from the outer needle hub 3 (see FIGS. 5 and 6), so that the operations can be carried out extremely readily. In addition, the inner needle 4 can be prevented from coming off from the protector 9 being in the state of covering the needle point 41.

Besides, since the first varied outside diameter section 42 and the reduced diameter part 915 are formed respectively in the inner needle 4 and the protector 9, the configuration is simple, and an increase in the number of component parts is obviated, which contributes to reductions in size and diameter.

Incidentally, the movement restraining means is not limited to such an engaging means. For example, the movement restraining means may be formed of a cord with a predetermined length for tying the inner needle hub 5 and the protector 9 to each other, a foldable or shrinkable tube with a predetermined length for tying the inner needle hub 5 and the protector 9 to each other so as to cover the inner needle 4, engagement between a projected part provided in one of the outside surface of the inner needle 4 and the inside wall of the inner needle passage 911 and a recessed part provided in the other, or the like.

In the indwelling needle assembly 1 as above-described, as shown in FIGS. 1 and 2, the tube 7 is connected to the base section of the outer needle hub 3, and the center axis $O_1$ of the outer needle 2 and the center axis $O_2$ of the tube 7 at its tip section are substantially parallel with each other in the assembled condition. In other words, the tube 7 protrudes from the base of the outer needle hub 3 in the base direction.

Here, if the tube 7 projects to a lateral side of the outer needle hub 3 (in the projecting direction of the vane 6a or 6b), the outer needle hub 3 is pulled in the lateral direction, i.e., in the direction in which the tube 7 projects from the outer needle hub 3, at the time of puncturing with the outer needle 2 and the inner needle 4, with the result that good balance is lost. In such a case, therefore, the intended operation is difficult to carry out.

Besides, if the tube 7 projects to the upper side of the outer needle hub 3 (in the direction substantially perpendicular to the projecting direction of the vane 6a or 6b), there is a possibility that the tube 7 is heavily bent (kinked) when the outer needle hub 3 is fixed to the patient at the time of causing the outer needle 2 to indwell in a patient's blood vessel or the like.

Further, if the tube 7 projects to the lateral side or the upper side of the outer needle hub 3, it is necessary to grip the inner needle hub 5 while avoiding the tube 7 so as not to pinch the tube 7, at the time of moving only the outer needle 2 forward in a blood vessel after the entering of the outer needle 2 into the blood vessel. Thus, the operation in this instance is troublesome.

On the other hand, in the indwelling needle assembly 1 according to the present invention, the tube 7 projects in the base direction of the outer needle hub 3, and is covered with the inner needle hub 5. Therefore, the above-mentioned inconveniences can be prevented from occurring, whereby excellent operationality is ensured.

Now, an example of the method of using the indwelling needle assembly 1 (in the case of puncturing a blood vessel) will be described in detail below.

[1] The indwelling needle assembly 1 is put into the assembled condition, and a connector mounted to an end of an infusion line is preliminarily connected to the connector 72, to enable an infusion liquid to be supplied from the infusion line.

Incidentally, in this instance, a predetermined portion of the tube 7 or on the infusion line is clamped, for example, by a clamp (an example of a conduit opening/closing means), thereby preliminarily closing the inner cavity.

[2] Next, the closure of the tube 7 or the infusion line by the clamp or the like is released, and the infusion liquid from the infusion line is introduced through the tube 7 into the outer needle hub 3.

The infusion liquid thus introduced into the outer needle hub 3 fills up the conduit 32, the conduit 82 and the space, on the tip side relative to the seal member 8, of the inside 31 of the outer needle hub 3, and is introduced into the inner cavity 21 of the outer needle 2. This results in priming of the inner cavity 21 of the outer needle 2 with the infusion liquid. In this case, a portion of the infusion liquid flows out through the tip opening 22 of the outer needle 2.

[3] When the priming is completed as above, the tube 7 or the infusion line is closed again by a clamp or the like, the vanes 6a and 6b are closed by pinching with fingers, and, with the vanes 6a and 6b as a grip part, the outer needle 2 and the inner needle 4 as one body are stuck into a patient's blood vessel (vein or artery).

By performing the puncturing operation into the blood vessel while gripping the vanes 6a and 6b, the puncture angle is reduced, i.e., the outer needle 2 and the inner needle 4 are closer to the state of being parallel with the blood vessel, as compared with the case where the puncturing operation is conducted by gripping the outer needle hub 3 directly. Therefore, the puncturing operation is easy to carry out, and the burden on the patient's blood vessel is alleviated.

When the blood vessel is captured by the outer needle 2, the blood flows back in the base direction inside the inner cavity 21 of the outer needle 2 via the groove 44 of the inner needle 4 due to the pressure inside the blood vessel (blood pressure). Therefore, this can be confirmed at least at one part of the outer needle 2, the outer needle hub 3, the inner needle hub 5 and the tube 7 having the property for permitting visual confirmation.

After the confirmation, the outer needle 2 and the inner needle 4 are further moved in the tip direction by a minute distance.

At the time of puncturing the blood vessel in this manner, the priming of the inner cavity 21 of the outer needle 2 with the infusion liquid has been completed, so that erroneous penetration of a bubble into the blood vessel is prevented assuredly, and extremely high safety is secured.

Besides, as above-mentioned, in the indwelling needle assembly 1 according to the present invention, the tube 7 is connected to the base section of the outer needle hub 3, and the center axis $O_1$ of the outer needle 2 and the center axis $O_2$ of the tube 7 at it tip section are substantially parallel with each other, in the assembled condition. Therefore, at the time of puncture with the outer needle 2 and the inner needle 4, the tube 7 would not serve as an obstacle, and excellent operationality is ensured.

[4] When the blood vessel is captured by the outer needle 2, either the outer needle 2 or the outer needle hub 3 is fixed by one hand, and the inner needle hub 5 is pulled in the base direction by gripping the inner needle hub 5 with the other hand, to withdraw the inner needle 4 from the outer needle 2.

[5] When the inner needle 4 is further moved in the base direction and the needle point 41 is passed through the hole 81, the seal member 8 having the self-closing property closes the hole 81 under its own elastic force. This ensures that leakage of the liquid through the hole 81 is obviated, and the asepsis of the inside of the outer needle hub 3 and the infusion line is secured.

[6] When the inner needle 4 is further moved in the base direction and the needle point 41 is passed through the vicinity of the recessed part 912 of the inner needle passage 911, the shutter member 921 is moved to the inner needle passage 911 side under the pressing force by the coil spring 922, and the right surface of the shutter member 921 is brought into contact with a surface opposed to the recessed part 912 of the inner needle passage 911. That is, the shutter means 92 is transferred from the first posture (see FIG. 2) to the second posture (see FIG. 3).

When the shutter means 92 is thus put into the second posture, the shutter member 921 closes the inner needle passage 911. Therefore, even if the needle point 41 returns in the tip direction again, the needle point 41 abuts on the shutter member 921 and cannot return.

[7] When the inner needle 4 is further moved in the base direction and the needle point 41 is passed through the vicinity of the through-hole 913 of the inner needle passage 911, the fixing pin 10 is moved toward the inner needle passage 911 side under the pressing force by the coil spring 12, and the right surface of the fixing pin 10 abuts on a surface opposed to the through-hole 913 of the inner needle passage 911. In this instance, a left end part of the fixing pin 10 comes off from the through-hole 35 of the outer needle hub 3. As a result, the fixation of the protector 9 to the outer needle hub 3 is released (see FIG. 4).

In the condition where the fixation of the protector 9 to the outer needle hub 3 is thus released, the shutter means 92 is operating assuredly; therefore, an accident such that the worker or the like erroneously pierce his finger or the like with the needle point 41 in discarding the inner needle 4 or the like occasion can be prevented more securely.

[8] When the inner needle 4 is further moved in the base direction, the first varied outside diameter section 42 cannot pass through the reduced diameter part 915, and is engaged with the reduced diameter part 915 (the inner needle 4 is engaged with the protector 9).

When the inner needle hub 5 is further pulled in the base direction in this condition, the protector 9 engaged with the inner needle 4 is moved in the base direction together with the inner needle 4, and is separated from the outer needle hub 3 (see FIGS. 5 and 6).

Incidentally, also at the time of carrying out the series of operations in the steps [5] to [9] as above, the center axis $O_1$ of the outer needle 2 and the center axis of the tube 7 on the tip side may be kept substantially parallel with each other, whereby the operations can be carried out smoothly and assuredly.

[9] Next, the tube 7 inserted in the inner needle hub 5 is detached through the slit 521 (see FIG. 7).

After the inner needle 4 is thus withdrawn from the outer needle 2, the inner needle 4 and the inner needle hub 5 are useless and, therefore, are discarded.

The inner needle 4 has its needle point 41 covered with the protector 9, and, particularly, the needle point 41 would not be moved toward the tip side beyond the shutter means 92 to protrude from the tip of the protector 9, and therefore the accident such that the worker at discarding work or the like person erroneously pierces his finger or the like with the needle point 41 is prevented.

[10] Next, the vanes 6a and 6b are opened, they are fixed to the patient's skin by use of a pressure sensitive adhesive tape or the like, the closure of the tube 7 or the infusion line by the clamp is released, and the supply of the infusion liquid is started.

The infusion liquid supplied from the infusion line is injected through the inner cavities of the connector 72, the tube 7, the outer needle hub 3 and the outer needle 2 into the patient's blood vessel.

While the indwelling needle assembly according to the present invention has been described above referring to the embodiment shown in the figures, the invention is not limited to the embodiment, and the component sections or parts of the indwelling needle assembly may be replaced with those of arbitrary configurations capable of displaying the same functions as above-mentioned. Besides, arbitrary components may be added to the embodiment.

In addition, the indwelling needle assembly according to the present invention is not limited to the one which is used for inserting in a blood vessel, and is applicable also to those used for inserting, for example, in the abdominal cavity, the thoracic cavity, a lymph vessel, the vertebral canal or the like.

In addition, there may be provided a cap which is mounted to the base section of the outer needle hub after the inner needle is withdrawn from the outer needle. This ensures that leakage of a liquid through the base of the outer needle hub can be prevented more securely. The cap may be formed as one body with the outer needle hub, or may be a separate body from the outer needle hub. Besides, the method for fixing the cap to the outer needle hub may be any method such as a method based on friction, a method based on hooking, etc.

In addition, the protector is not limited to the one configured as shown in the accompanying figures. For example, the protector may be one which is so provided as to be turnable (displaceable) between a position where it covers at least the needle point of the inner needle and a position where it is spaced away from the inner needle.

INDUSTRIAL APPLICABILITY

The indwelling needle assembly according to the present invention includes: an inner needle having a sharp point at its tip; an inner needle hub fixed to a base section of the inner needle; a hollow outer needle into which the inner needle is inserted; an outer needle hub fixed to the base of the outer needle; and a tube inserted into the inner needle hub and connected to the base section of the outer needle hub so that the inner cavity of the tube communicates with the inner cavity of the outer needle, wherein the center axis of the outer needle and the center axis of the tube at its head section are substantially parallel with each other in the condition where the inner needle is inserted in the outer needle. Therefore, the tube does not serve as an obstacle at the time of the puncturing operation, so that excellent operationality is ensured, and a line for an infusion liquid or the like can be captured easily and assuredly. Accordingly, the indwelling needle assembly of the present invention has industrial applicability.

The invention claimed is:
1. An indwelling needle assembly comprising:
an inner needle having a sharp point at a tip thereof;
an inner needle hub fixed to a base section of said inner needle;
a hollow outer needle into which said inner needle is inserted;
an outer needle hub fixed to a base section of said outer needle;
a tube inserted into said inner needle hub and connected to said base section of said outer needle hub so that an inner cavity of said tube communicates with an inner cavity of said outer needle; and
a protector for covering at least said sharp point of said inner needle when said inner needle is withdrawn from said outer needle;
wherein a center axis of said outer needle and a center axis of said tube at a head section of said tube are substantially parallel with each other in the condition where said inner needle is inserted into said outer needle, wherein said protector is at least partially covered with at least one of the inner needle hub and the outer needle hub in an assembled condition, and wherein said inner needle hub is provided with a slit along a longitudinal direction thereof so that said tube can be detached from said inner needle hub through said slit when said inner needle is withdrawn from said outer needle.

2. The indwelling needle assembly as set forth in claim 1, further comprising a seal member provided at said outer needle hub, provided with a hole into which said inner needle can be inserted, and having a self-closing property such that said hole closes upon withdrawal of said inserted inner needle.

3. The indwelling needle assembly as set forth in claim 2, wherein said inner needle has a section differing in an outside diameter; and a smallest outside diameter section of said inner needle is located in said hole of said seal member in the condition where said inner needle is inserted in said outer needle.

4. The indwelling needle assembly as set forth in claim 1, wherein said inner cavity of said outer needle and said inner cavity of said tube communicate with each other through a junction conduit provided in said outer needle hub.

5. The indwelling needle assembly as set forth in claim 1, wherein said protector includes a protector body having an inner needle passage into which said inner needle can be inserted, and shutter means which is displaced between a first posture such that said inner needle can be inserted into said inner needle passage and a second posture to inhibit the passage of said point of said inner needle.

6. The indwelling needle assembly as set forth in claim 1, further comprising movement restraining means for restraining said inner needle from moving in the direction opposite to said point of said inner needle in relation to said protector in the condition where said protector covers at least said point of said inner needle.

7. The indwelling needle assembly as set forth in claim 6, wherein said movement restraining means comprises engaging means for engagement between said inner needle and said protector.

8. The indwelling needle assembly as set forth in claim 7, wherein said inner needle has a section differing in an outside diameter;

said protector body has a reduced diameter section where an inside diameter of said inner needle passage is reduced; and said engaging means comprises said section with a varying outside diameter of said inner needle and said reduced diameter section.

9. The indwelling needle assembly as set forth in claim 1, wherein a conduit providing communication between a tip opening of said outer needle and an inside of said outer needle hub is formed in at least a part, making close contact with said outer needle, of an outer peripheral portion of said inner needle in the condition where said inner needle is inserted into said outer needle.

10. The indwelling needle assembly as set forth in claim 1, wherein said inner needle is solid.

* * * * *